(12) United States Patent
Beletsky

(10) Patent No.: US 12,359,171 B2
(45) Date of Patent: Jul. 15, 2025

(54) METHOD FOR PRODUCING NK CELLS WITH PD-1 KNOCKOUT GENE AND TRAIL OR FAS-LIGAND OVEREXPRESSION

(71) Applicant: Igor Petrovich Beletsky, Helsinki (FI)

(72) Inventor: Igor Petrovich Beletsky, Chicago, IL (US)

(73) Assignee: Igor Beletsky, Helsinki (FI)

( * ) Notice: Subject to any disclaimer, the term of this patent is extended or adjusted under 35 U.S.C. 154(b) by 937 days.

(21) Appl. No.: 17/602,929

(22) PCT Filed: Apr. 9, 2020

(86) PCT No.: PCT/RU2020/000188
§ 371 (c)(1),
(2) Date: Oct. 11, 2021

(87) PCT Pub. No.: WO2020/209759
PCT Pub. Date: Oct. 15, 2020

(65) Prior Publication Data
US 2022/0288117 A1 Sep. 15, 2022

(30) Foreign Application Priority Data
Apr. 12, 2019 (RU) ................. 2019111060

(51) Int. Cl.
| | |
|---|---|
| *C12N 5/0783* | (2010.01) |
| *A61K 40/15* | (2025.01) |
| *A61K 40/42* | (2025.01) |
| *A61P 35/00* | (2006.01) |
| *C12N 9/22* | (2006.01) |
| *C12N 15/85* | (2006.01) |

(52) U.S. Cl.
CPC ............ *C12N 5/0646* (2013.01); *A61K 40/15* (2025.01); *A61K 40/421* (2025.01); *A61P 35/00* (2018.01); *C12N 9/22* (2013.01); *C12N 15/85* (2013.01); *C12N 2310/20* (2017.05); *C12N 2510/00* (2013.01)

(58) Field of Classification Search
None
See application file for complete search history.

(56) References Cited

U.S. PATENT DOCUMENTS

| 10,640,574 B2 * | 5/2020 | Bazirgan | .......... C07K 14/43522 |
| 2018/0171298 A1 * | 6/2018 | Duchateau | ..... A61K 39/464499 |

FOREIGN PATENT DOCUMENTS

| CN | 102229962 A | * | 11/2011 |
| CN | 107586777 A | | 1/2018 |
| CN | 108753817 A | | 11/2018 |
| WO | WO2001027254 A2 | * | 4/2001 |
| WO | 2017/001572 A1 | | 1/2017 |
| WO | 2017093969 A1 | | 6/2017 |
| WO | 2017193107 A2 | | 11/2017 |
| WO | 2017214569 A1 | | 12/2017 |
| WO | 2019063018 A1 | | 4/2019 |

OTHER PUBLICATIONS

Xue W, et al. (2019) Anti-PD1 upregulates PD-L1 expression and inhibits T-cell lymphoma progression: possible involvement of an IFN-γ-associated JAK-STAT pathway, OncoTargets and Therapy, , 2079-2088, DOI: 10.2147/OTT.S187280 (Year: 2019).*
Machine Translation of CN102229962A Description. Espacenet. Downloaded Apr. 11, 2025. (Year: 2025).*
International Search Report and Written Opinion dated Oct. 8, 2020, from corresponding International No. PCT/RU2020/000188.
Emily, Pomeroy et al. "Enhancing Human NK Cell Function and Specificity for Cancer Immunotherapy." Blood, 2018, 132, Supplement 1, 703. Adoptive Immunotherapy, Poster I: 2044, pp. 1-7.
Hsu, Joy et al., "Contribution of NK cells to immunotherapy mediated by PD-1/PD-L1 blockade." The Journal of Clinical Investigation, 2018, 128(10): pp. 4654-4668.
Van Bloke et al., "Methods to create a stringent selection system for Mammalian cell lines." Cytotechnology, 2011, 63: pp. 371-384.
European Patent Office, European Search Report and Opinion issued on Dec. 15, 2023 in corresponding European Application No. 20788293.7, 9 pages.
Guo, X. et al. "Disruption of PD-1 Enhanced the Anti-tumor Activity of Chimeric Antigen Receptor T Cells Against Hepatocellular Carcinoma", Frontiers in Pharmacology, vol. 9, 15 pages (Oct. 1, 2018).
Zhang, C. et al. "Genetic abrogation of immune checkpoints in antigen-specific cytotoxic T-lymphocyte as a potential alternative to blockade immunotherapy", Scientific Reports 8:5549, 13 pages (2018).

* cited by examiner

*Primary Examiner* — Allison M Fox
*Assistant Examiner* — Alyssa G Weston
(74) *Attorney, Agent, or Firm* — Espatent Oy

(57) ABSTRACT

The invention relates to the field of medicine and genetic engineering, specifically to guide RNAs and DNA fragments and to cell selection methods, which can be used in CRISPR-Cas9 systems for producing lines of natural killer cells with a PD-1 knockout gene and increased production of TRAIL or Fas-ligand proteins. Methods are disclosed for producing modified lines of NK cells: with a PD-1 knockout gene and constitutive Fas-ligand overexpression, with a PD-1 knockout gene and constitutive TRAIL overexpression, and also a method is described for selecting modified NK cells with a PD-1 knockout gene, which is carried out using a zeocin selection marker. The invention makes it possible to produce a high yield of modified lines of NK cells that are highly active in inhibiting the growth of tumour cells.

Figure 1:
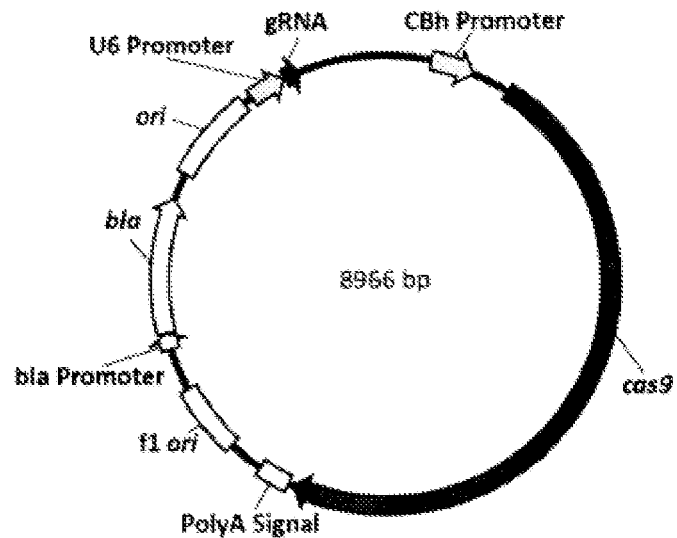

9 Claims, 5 Drawing Sheets
Specification includes a Sequence Listing.

METHOD FOR PRODUCING NK CELLS WITH PD-1 KNOCKOUT GENE AND TRAIL OR FAS-LIGAND OVEREXPRESSION

TECHNICAL FIELD

The invention relates to medicine and genetic engineering, in particular to guide RNA and DNA fragments and methods of cell selection that can be used in CRISPR-Cas9 systems to obtain natural killer cell lines with a PD-1 knockout gene and increased production of TRAIL or Fas-ligand proteins.

PRIOR ART

Methods for treating cancer with monoclonal antibodies have been developed since the late 1970s, having become the main direction for immunotherapy based on the use of certain connections in the immune system to fight a tumor. Immunotherapy has advantages, but immunotherapeutic drugs which have been developed are not universal and are better suited for some types of cancer than others. Some monoclonal antibodies enhance the immune response to cancer cells by attaching to them as a signaling beacon. One example is the drug alemtuzumab which binds to the CD52 antigen present on lymphocytes and which is prescribed for chronic lymphocytic leukemia. Others block tumor antigens, interfering with cell growth and reproduction, such as trastuzumab, which is an antibody against the HER2 surface protein and helps prevent the growth of stomach and breast tumors. A third subgroup of monoclonal antibodies targets immune checkpoints.

One of the most promising approaches to activating internal forces to fight cancer is connected to the use of monoclonal antibodies that block the interaction of PD-1 and PD-L1 proteins which masks cancer cells as healthy ones. There are two known anti-PD-1 monoclonal antibodies. One is made by MSD, the other by Bristol-Myers Sqibb. After neutralization of PD-1, the body begins to recognize tumor cells as foreign and destroy them. Monoclonal antibodies to PD-1 have great therapeutic potential for the treatment of not only melanoma, but also non-small cell lung cancer and renal cell carcinoma.

The prior art knows Japanese patent JP6157574 (Jul. 5, 2017) and Korean application No. KR20180093990, published on Aug. 22, 2018, which consider methods of making monoclonal antibodies to PD-1 and a new therapeutic strategy for anti-PD-1 antibody therapy [1].

Other technical solutions are based on the use of a combination of PD-1 inhibitors. The invention in US2016222121 (Aug. 4, 2016) describes methods of treating hematologic cancers using a combination of PD-1 or PD-L1 inhibitors and TIM-3, LAG-3 or CTLA-4. In one embodiment, a PD-1 or PD-L1 inhibitor is administered in combination with a TIM-3 inhibitor. In another embodiment, a PD-1 or PD-L1 inhibitor is administered in combination with a LAG-3 inhibitor. In yet another embodiment, a PD-1 or PD-L1 inhibitor is administered in combination with a CTLA-4 inhibitor [2].

Another approach involves the use of bispecific monoclonal antibodies. These drugs are made up of parts of two different monoclonal antibodies, thanks to which they can simultaneously attach to two different proteins. One example is the drug blinatumomab for the treatment of a rare form of acute lymphocytic leukemia. One part of the drug molecule binds to CD19, which is found in some leukemia and lymphoma cells, while the other part has an affinity for the CD3 protein found in normal T-cells of the immune system.

The prior art knows application EP3382009 (Oct. 3, 2018), in which the chimeric antigen-receptor-modified immune effector cell PD-L1 blocking agent may include: soluble PD-1; a soluble PD-1 fusion peptide and a hIgG4el-Fc CH3 domain; a fusion peptide of soluble PD-1 and hIgG4el-Fc; or a specific antibody anti-PD-L1 [3].

Djoke Hendriksa et al. [4] describes preparation and study of the use of the anti-PD-L1:TRAIL protein containing a fragment of the PD-L1-blocking antibody genetically fused with the extracellular domain TRAIL (tumor necrosis factor-related apoptosis-induced ligand), which belongs to the TNF family and is the second type of membrane protein. TRAIL implements apoptosis by interacting with death receptors. Unlike other cytokines, it interacts with a complex of receptors: pro-apoptotic, death receptors, and anti-apoptotic. Testing the anti-PD-L1:TRAIL fusion protein showed an increase in T-cell activation, resulting in increased killing of cancer cell lines and major patient-derived cancer cells in mixed T-cell/cancer cell culture experiments.

The use of monoclonal and bifunctional antibodies is associated with many side effects, since antibodies are proteins that cause at least allergic reactions.

Approaches are known to the treatment of tumors based on the local use of delivery vectors, which achieve a high level of expression in the tumor environment. In the work of Modiano J F [5], the prospect of using Fas-ligand in immunotherapy is considered. Fas ligand (FasL, CD95L) is a type II 40-KDA transmembrane protein that binds to the FAS (CD95 phenotype) receptor and promotes programmed cell death. The use of FasL has been shown to induce a systemic antitumor response that delays or prevents progression and simultaneously attacks distant metastases.

Currently, there is active development of T-cells expressing new third generation chimeric receptors. The prior art knows Chinese application No. CN103820454 (May 28, 2014) and the article by Su S. et al. published 2016 Jan. 28 [6,7], which describes a method for knocking out the human PD1 gene using the CRISPR-Cas9 genome editing system in T-cells. The invention relates to a method for specific knockout of the human PD1 gene using CRISPR-Cas9 (clustered regular interspaced short palindromic repeat) and sgRNA (unidirectional RNA) in human T-cells for the treatment of cancer patients.

Clinical data on the use of CAR T-cells in cancer treatment have shown promising results [8]. However, there is a high risk to the patient, and some patients' T-cells are not effective enough for treatment even after TCR or CAR redirection, causing allogeneic donor T-cell modification. This approach is limited by the time and cost of producing patient-specific T-cell products. Therefore, there is a demand for safer ways to modify cells, bypassing the time and cost of producing patient-specific T-cell products.

These disadvantages are eliminated by using natural killer cells. Natural killer cells (NK-cells) are characterized as lymphocytes of innate immunity, possessing antiviral and antitumor cytotoxic activity. By means of a set of NK-cell receptors, cells recognize molecules on the cell surface, the expression of which indicates viral infection, tumor formation or damage caused by cellular stress [9,10,11].

The prior art knows the invention of O'Dwyer M., "Modified natural killer cells and natural killer cell lines having increased cytotoxicity" proposed in U.S. Pat. No. 10,034,925 (Jul. 31, 2018), in which, in order to increase cytotoxicity in the treatment of cancer, NK-cells are genetically modified to remove expression checkpoints selected from inhibitory receptors, for example PD1, and modified to increase the expression of the mutant variant of the TRAIL ligand [12].

The object of the present invention is to develop new genetic structures that increase the effectiveness of tumor treatment using new types of natural killer cells, which expand the arsenal of new therapeutic agents.

The technical result consists in the fact that the claimed methods (variants) of obtaining a modified line of NK-cells with a knockout PD-1 gene make it possible to increase the efficiency of apoptosis or lysis of mammalian cancer cells.

The claimed methods of application make it possible to expand the range of use of the developed genetically engineered constructs of modified NK-cell lines to increase the effectiveness of treatment in mammals.

About the Invention

One aspect of the invention is a method of producing a modified NK-cell line with a knockout PD-1 gene in order to induce apoptosis or lysis of mammalian cancer cells. At the same time, to inactivate the expression of the PD-1 gene, guide RNA sequences specific to various sites of the PD-1 gene included in the group SEQ ID NO: 1, SEQ ID NO: 2, SEQ ID NO: 3, SEQ ID NO: 4 are selected, expression plasmid vectors are constructed encoding the selected guide RNA and endonuclease Cas9, the culture of NK-cells is transfected with one of the plasmid vectors, cells are stained with anti-PD-1 antibodies, cloning and selection are carried out, secondary cultivation of cell clones and selection cells is carried out using immunoblotting with anti PD-1 antibodies. In this case, the composition of the plasmid vector with the physical map shown in FIG. 1 includes: 295-572 bp—CBh promoter; 819-5090 bp—Cas9 endonuclease; 5121-5328 bp—PolyA Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

Another aspect of the present invention is the use of a modified NK-cell line with a knockout PD-1 gene to induce apoptosis or lysis of mammalian cancer cells, comprising administering to the mammal an effective amount of a killer (NK) cell.

The next aspect of the present invention is a method for selecting a modified NK-cell line with a knockout PD-1 gene, which is carried out using the selective marker zeocin, wherein to inactivate the expression of the PD-1 gene, guide RNA sequences specific to different sites of the PD-1 gene are selected and included in the group SEQ ID NO: 1, SEQ ID NO: 2, SEQ ID NO: 3, SEQ ID NO: 4, expression plasmid vectors are selected, encoding the selected guide RNA and Cas9 endonuclease, a fragment of donor DNA is synthesized, encoding an expression cassette for resistance of cells to zeocin, having the sequence according to SEQ ID NO: 9, the culture of NK-cells is transfected with a mixture of the plasmid vector and a fragment of donor DNA, the cells are cultured in a selective medium with zeocin, the surviving cells are stained with anti-PD-1 antibodies, cells are selected and cloned with a minimum signal using a flow sorter, secondary culturing of cell clones and selection of cells is carried out by immunoblotting with anti PD-1 antibodies. In this case, the composition of the plasmid vector with the physical map shown in FIG. 1 includes: 295-572 bp—CBh promoter; 819-5090 bp—Cas9 endonuclease; 5121-5328 bp—PolyA Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

At the same time, the donor DNA with a size of 2.371 kb, which inactivates the expression of the PD-1 gene with simultaneous activation of the expression in the NK-cell of the zeocin protein, includes: a fragment containing the sequence of the first part of the pd1 gene with a size of 379 base pairs, characterized by a nucleotide sequence, shown in SEQ ID NO: 10; a fragment containing the sequence of CMV enhancer with a size of 405 base pairs, characterized by the nucleotide sequence shown in SEQ ID NO: 11; a fragment containing the sequence-hFerL Promoter with a size of 263 base pairs, characterizing the nucleotide sequence shown in SEQ ID NO: 12; a fragment containing the sequence-Zeo-zeocin resistance gene with a size of 375 base pairs, characterized by the nucleotide sequence shown in SEQ ID NO: 13; a fragment containing the sequence βGlo polyA Signal with a size of 401 base pairs, characterized by the nucleotide sequence shown in SEQ ID NO: 14; and a fragment containing the sequence of the second part of the pd1 gene with a size of 276 base pairs and characterized by the nucleotide sequence shown in SEQ ID NO: 15.

Another aspect of the present invention is a method for producing a modified NK-cell line with a knockout PD-1 gene and constitutively increased expression of the Fas-ligand, in which, to inactivate the expression of the PD-1 gene, guide RNA sequences specific to different sites of the PD-1 gene are selected and included in the group SEQ ID NO: 1, SEQ ID NO: 2, SEQ ID NO: 3, SEQ ID NO: 4, expression plasmid vectors are construed, encoding the selected guide RNA and Cas9 endonuclease, a fragment of donor DNA is synthesized, encoding an expression cassette for the Fas-ligand, having the sequence according to SEQ ID NO: 16, the culture of NK-cells is transfected with a mixture of the plasmid vector and the donor DNA fragment, the cells are cultured, the surviving cells are stained with anti-PD-1 antibodies and anti-Fas-ligand antibodies, selection and cloning of cells is carried out with a minimum signal for PD-1 and a maximum signal for Fas-ligand using a flow sorter, and secondary culturing of cell clones and selection of cells are carried out using immunoblotting with anti PD-1 antibodies and anti Fas-ligand antibodies.

In this case, the composition of the plasmid vector with the physical map shown in FIG. 1 includes: 295-572 bp—CBh promoter; 819-5090 bp—Cas9 endonuclease; 5121-5328 bp—PolyA Signal; 5552-6007 bp—P ori; 6289-6393 bp—bla promoter; 6394-7254 bp—bla; 7425-8013 bp—ColE1 ori; 8075-8315 bp—U6 promoter; 8322-8419 bp—sequence encoding a guide RNA. Wherever the donor DNA with a size of 2.473 kb, providing inactivation of the expression of the PD-1 gene with simultaneous activation of expression in the NK-cell of the Fas-ligand protein includes: a fragment containing the sequence of the first part of the pd1 gene with a size of 379 base pairs, characterized by the nucleotide sequence shown in SEQ ID NO: 10; a fragment containing the sequence CMV Promoter with a size of 588 base pairs, characterized by the nucleotide sequence shown in SEQ ID NO: 17; a fragment containing the sequence Fas-ligand with a size of 846 base pairs characterized by the nucleotide sequence shown in SEQ ID NO: 18; a fragment containing the sequence BGH polyA Signal with a size of 225 base pairs, characterized by the nucleotide sequence shown in SEQ ID NO: 19; and a fragment containing the sequence of the second part of the pd1 gene with a size of 276 base pairs, characterized by the nucleotide sequence shown in SEQ ID NO: 15.

A further aspect of the present invention is the use of a modified NK-cell line with a knockout PD-1 gene and constitutively increased Fas-ligand expression to induce apoptosis or lysis of mammalian cancer cells, comprising administering to the mammal an effective amount of a killer (NK) cell.

Another aspect of the present invention is a method of producing a modified NK-cell line with a knockout PD-1 gene and constitutively increased TRAIL expression in order to induce apoptosis or lysis of mammalian cancer cells. Wherever, in order to inactivate the expression of the PD-1 gene, guide RNA sequences specific to various sites of the PD-1 gene included in the group SEQ ID NO: 1, SEQ ID NO: 2, SEQ ID NO: 3, SEQ ID NO: 4 are selected, expression plasmid vectors are constructed encoding the selected guide RNA and endonuclease Cas9, a fragment of donor DNA is synthesized encoding an expression cassette for TRAIL having the sequence according to SEQ ID NO: 20, the culture of NK-cells is transfected with a mixture of the plasmid vector and a fragment of donor DNA, cell culture is carried out, surviving cells are stained with anti-PD-1 antibodies and anti-TRAIL antibodies, the selection and cloning of cells is carried out with a minimum signal for PD-1 and a maximum signal for TRAIL using a flow sorter, and secondary culturing of cell clones and selection of cells are carried out using immunoblotting with anti PD-1 antibodies and anti-TRAIL antibodies. In this case, the composition of the plasmid vector with the physical map shown in FIG. 1 includes: 295-572 bp—CBh promoter; 819-5090 bp, Cas9 endonuclease; 5121-5328 bp—PolyA Signal; 5552-6007 bp—flori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

At the same time, the donor DNA with a size of 2.473 kb, providing inactivation of the PD-1 gene expression with simultaneous activation of TRAIL protein expression in the NK-cell, includes: a fragment containing the sequence of the first part of the pd1 gene with a size of 379 base pairs, characterized by a nucleotide sequence presented in SEQ ID NO: 10; a fragment containing the sequence CMV Promoter with a size of 588 base pairs, characterized by the nucleotide sequence shown in SEQ ID NO: 17; a fragment containing the sequence TRAIL with a size of 846 base pairs, characterized by the nucleotide sequence shown in SEQ ID NO: 21; a fragment containing the sequence BGH polyA Signal with a size of 225 base pairs, characterized by the nucleotide sequence shown in SEQ ID NO: 19; and a fragment containing the sequence of the second part of the pd1 gene with a size of 276 base pairs, characterized by the nucleotide sequence shown in SEQ ID NO: 15.

A further aspect of the present invention is the use of a modified line of NK-cells with the PD-1 gene knocked out and constitutively increased expression of TRAIL in order to induce apoptosis or lysis of mammalian cancer cells, comprising administering to a mammal an effective amount of a killer (NK) cell.

LIST OF FIGURES

FIG. 1. Physical map of the plasmid vector, which includes: 295-572 bp—CBh promoter; 819-5090 bp—Cas9 endonuclease 5121-5328 bp—PolyA Signal; 5552-6007 bp—fl ori; 6289-6393 bp—bla promoter; 6394-7254 bp—bla; 7425-8013 bp—ColE1 ori; 8075-8315 bp—U6 promoter; 8322-8419 bp—guide RNA (gRNA) coding sequence.

Figure 2:
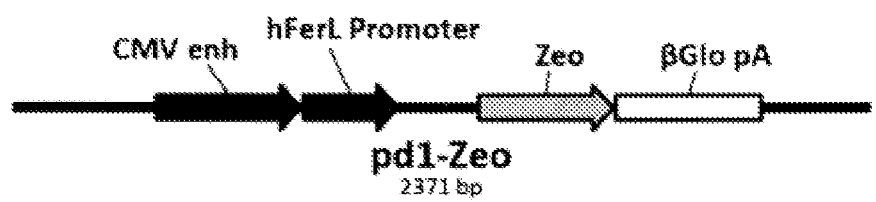

FIG. 2. Map of the pd1-Zeo donor DNA fragment. Where: 1-379 bp—sequence of a part of the pd1 gene SEQ ID NO: 10; 395-799 bp—CMV enh enhancer SEQ ID NO: 11; 806-1068 bp—hFerL Promoter SEQ ID NO: 12; 1291-1665 bp—Zeo-Zeocin resistance gene SEQ ID NO: 13; 1673-2073 bp—βGlo polyA Signal SEQ ID NO: 14; and 2096-2371 bp—sequence of a portion of the pd1 gene SEQ ID NO: 15.

Figure 3:
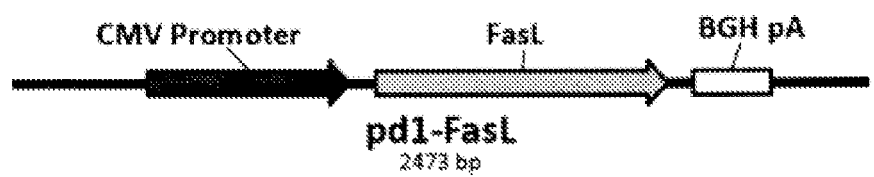

FIG. 3. Map of the pd1-FasL donor DNA fragment. Where: 1-379 bp—sequence of a part of the pd1 gene SEQ ID NO: 10; 389-976 bp—CMV Promoter SEQ ID NO: 17; 1052-1897 bp—FasL SEQ ID NO: 18; 1969-2193 bp—BGH polyA Signal SEQ ID NO: 19; 2198-2473 bp—sequence of a portion of pd1 gene SEQ ID NO: 15.

Figure 4:
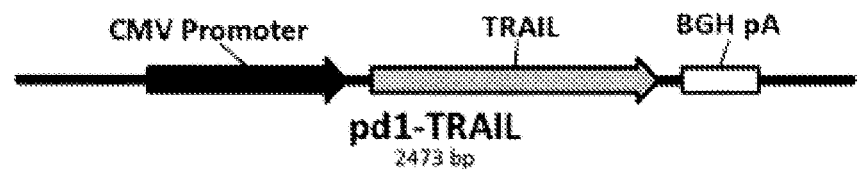

FIG. 4. Map of the pd1-TRAIL donor DNA fragment. Where: 1-379 bp—sequence of a part of the pd1 gene SEQ ID NO: 10; 389-976 bp—CMV Promoter SEQ ID NO: 17; 1052-1897 bp—TRAIL SEQ ID NO: 21; 1969-2193 bp—BGH polyA Signal SEQ ID NO: 19; 2198-2473 bp—sequence of a portion of pd1 gene SEQ ID NO: 15.

Figure 5:
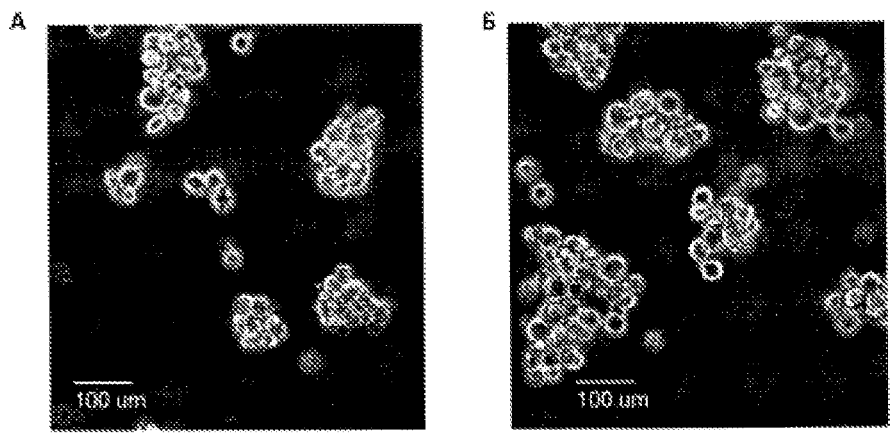

FIG. 5 Micrographs of NK92 (A) and NK92-PD1 (B) cell lines incubated with K562 target cells at a 3:1 ratio for 6 hours.

Figure 6:
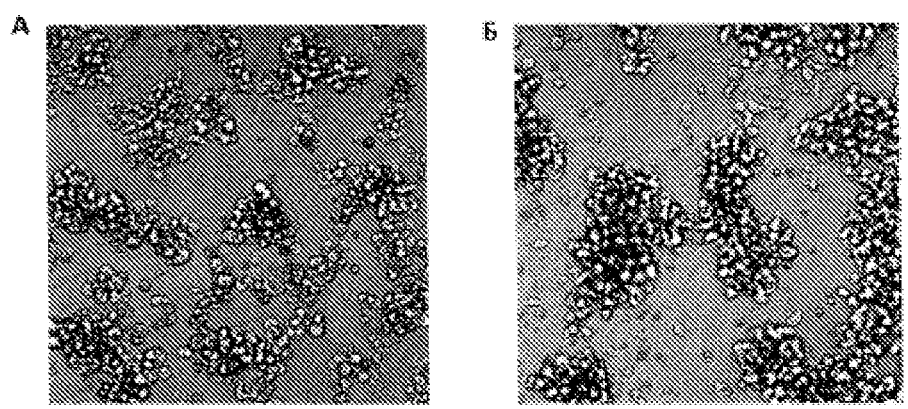

FIG. 6 Micrographs of NK92 (A) and NK92-PD1 (B) cell lines incubated with HeLa target cells at a ratio of 3:1 for 6 hours.

Figure 7:
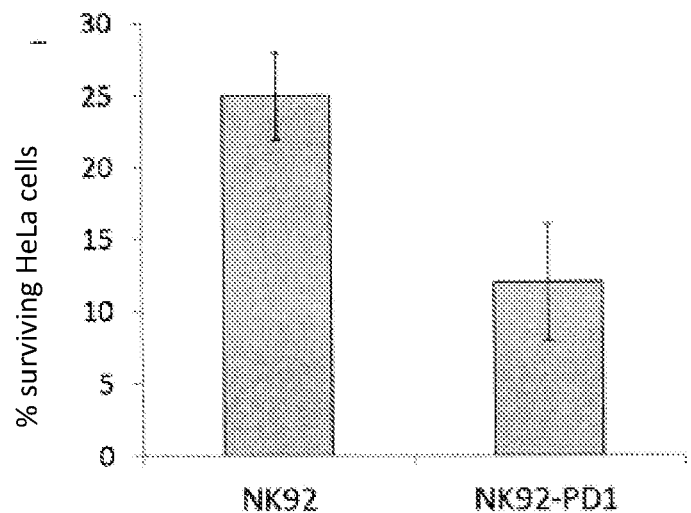

FIG. 7 Percentage of surviving HeLa target cells after incubation with NK92 and NK92-PD1 cells for 6 hours. Data are presented as the mean value of three experiments.

Figure 8:
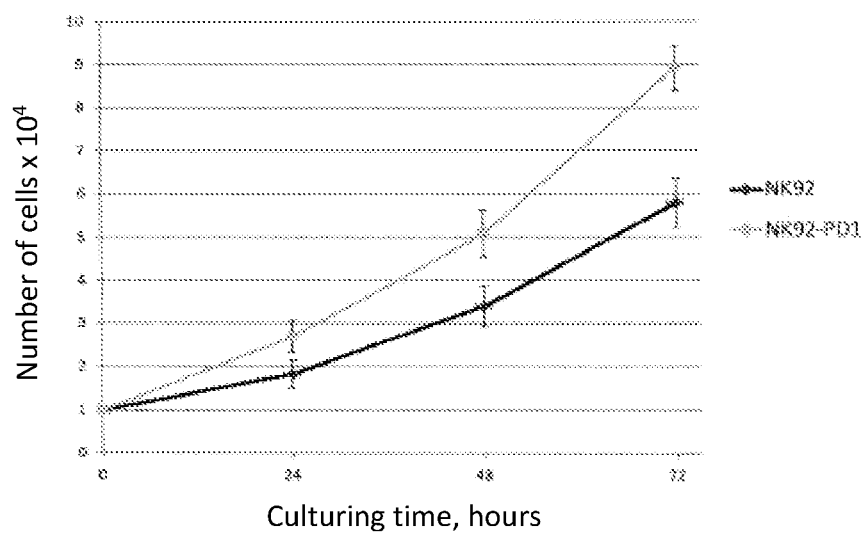

FIG. 8 Comparative growth kinetics of NK92 and NK92-PD1 cell cultures. Data are presented as the mean of three experiments.

Figure 9:
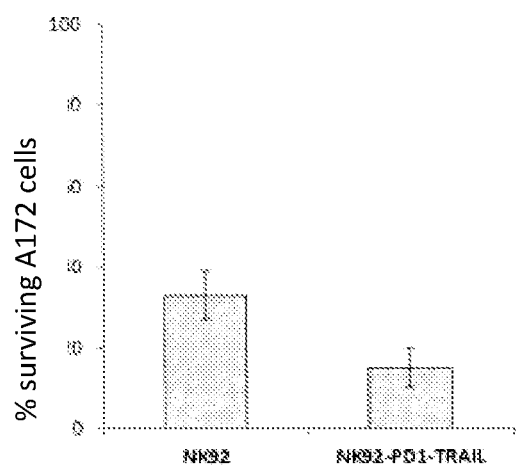

FIG. 9 Percentage of surviving A172 target cells after 6 hours of cultivation in the presence of NK92 or NK92-PD1-TRIAL. Data are presented as the mean of three experiments.

Figure 10:
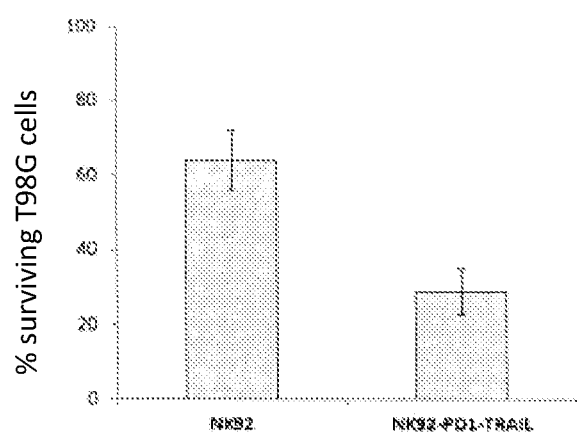

FIG. 10 Percentage of surviving T98G target cells after 8 hours of culture in the presence of NK92 or NK92-PD1-TRIAL. Data are presented as the mean of three experiments.

INVENTION DESCRIPTION

The present invention relates to a cell or NK-cell line of natural killer (NK) cells that have been genetically modified in such a way as to increase their cytotoxicity.

These NK-cells and NK-cell lines can be: a) isolated from peripheral blood, b) isolated from umbilical cord blood, c) obtained from pluripotent and embryonic stem cells (i.e. iPSCs and ESC) using the method of Galat et al [9.10], d) obtained from pluripotent stem cells (iPSCs) using the method of Kaufman et al. [11]. These NK-cells and NK-cell lines can be infiltrated into tissues and tumors. These NK-cells and NK-cell lines can be included in the group consisting of KHYG-1/CVCL_2976, NK-92/CVCL_2142, NK-YS/CVCL_8461, NKL/CVCL_0466, and NK3.3/CVCL_7994, which includes but is not limited to other types of NK-cells and NK-cell lines.

Generation of PD-1 Knockout NK-Cells

The method for obtaining a line of PD-1 knockout NK-cells includes several main steps:
 1. Selection of a guide RNA sequence specific to various sites of the PD-1 gene having a sequence according to SEQ ID NO: 1 or SEQ ID NO: 2 or SEQ ID NO: 3 or SEQ ID NO: 4;

2. Construction of an expression plasmid vector encoding the selected guide RNA and Cas9 endonuclease (pGR301 or pGR302 or pGR303 or pGR304);

The composition of the plasmid vector with a physical map shown in FIG. 1 includes: 295-572 bp—CBh promoter; 819-5090 bp—Cas9 endonuclease; 5121-5328 bp—PolyA Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

3. Transfection of a culture of NK-cells with one of the plasmid vectors;
4. Cell staining with anti-PD-1 antibodies, selection and cloning of cells with a minimal signal using a flow sorter.
5. Culturing of clones of cells, and secondary selection of cells by immunoblotting with anti-PD-1 antibodies.

To select the optimal guide RNA sequences, the analysis of nucleotide sequences was carried out using freely available web resources: CRISPR Design, CHOPCHOP, E-CRISPR. Sequences of guide RNAs were selected having sequences according to SEQ ID NO: 1-4, specific to various sites of the PD-1 gene having a sequence according to SEQ ID NO: 5-8.

```
In vector pGR301 of SEQ ID NO: 1
GTCTGGGCGGTGCTACAACTGTTTTAGAGCTAGAAATAGCAAGTTAAAAT

AAGGCTAGTCCGTTATCAACTTGAAAAAGTGGCACCGAGTCGGTGC

In vector pGR302 of SEQ ID NO: 2
GGGCGGTGCTACAACTGGGCGTTTTAGAGCTAGAAATAGCAAGTTAAAAT

AAGGCTAGTCCGTTATCAACTTGAAAAAGTGGCACCGAGTCGGTGC

In vector pGR303 of SEQ ID NO: 3
GGCGCCCTGGCCAGTCGTCTGTTTTAGAGCTAGAAATAGCAAGTTAAAAT

AAGGCTAGTCCGTTATCAACTTGAAAAAGTGGCACCGAGTCGGTGC

In vector pGR304 of SEQ ID NO: 4
GCCCTGGCCAGTCGTCTGGGGTTTTAGAGCTAGAAATAGCAAGTTAAAAT

AAGGCTAGTCCGTTATCAACTTGAAAAAGTGGCACCGAGTCGGTGC.

Target DNA sequences
(PAM sequences highlighted):
For vector pGR301 of SEQ ID NO: 5
GTCTGGGCGGTGCTACAACTGGG For vector pGR302 of SEQ ID NO: 6
GGGCGGTGCTACAACTGGGCTGG For the pGR303 vector SEQ ID NO: 7
GGCGCCCTGGCCAGTCGTCTGGG For vector pGR304 of SEQ ID NO: 8
GCCCTGGCCAGTCGTCTGGGCGG
```

To obtain plasmid vectors encoding complexes of Cas9 endonuclease and guide RNAs, DNA fragments encoding guide RNAs were synthesized using a polymerase chain reaction with overlapping oligonucleotides. The resulting fragments were cloned into a plasmid vector intended for the expression of the components of the CRISPR-Cas9 system in mammalian cells. The vector was pre-digested at the BbsI restriction endonuclease site. Selected plasmid vectors pGR301, pGR302, pGR303, and pGR304 were sequenced to confirm that the planned genetic constructs were obtained.

NK-cells were transfected with pGR301, pGR302, pGR303, and pGR304 vectors using Lipofectamine 3000 (Thermo Fisher Scientific), cells were incubated in an RPMI medium with 20% fetal bovine serum until a cell density of 4 6×10$^5$ cells/ml was reached. A mixture of Lipofectamine 3000 lipagent and DNA was prepared (at a ratio of 3 μL lipagent, 4 μg pGR301 or pGR302 or pGR303 or pGR304, 8 μL P3000™ reagent, and 100 μL Opti-MEM® Medium per 1 ml cell suspension). The mixture was incubated for 5 min and added to the cell suspension. The cells were incubated for 48 h at 37° C. and 5% CO2.

To select PD-1 gene knockout cells 48 h after transfection, the cells were incubated with anti-PD-1 antibodies labeled with fluorescein for 1 h. The cells were washed with a culture medium and separated using a cell sorter. Single cells with minimal or no fluorescent signal were selected in the wells of a 96-well plate with the RPMI medium with 20% fetal bovine serum. The cells were cultured for 2-4 weeks at 37° C. and 5% CO2 with replacement of the culture medium every 3-4 days.

To obtain labeled anti-PD-1 antibodies, we used monoclonal mouse anti-PD-1 antibodies, the clone NAT105 (Manufacturer: Abcam cat. no. ab52587) and Fluorescein-EX Protein Labeling Kit (Manufacturer Invitrogen™, cat. no. F10240).

The expression level of PD-1 in the clones was assessed using immunoblotting with anti-PD-1 antibodies. Non-transfected NK-cells were used as a positive control. The cells were lysed using a buffer containing 25 mM Tris-HCl, 150 mM NaCl, mMEDTA, and 1% Triton-X100. Cell lysates were centrifuged at 10,000 g for 10 min. The concentration of total protein in the supernatant was determined and aliquots corresponding to 100 μg of protein were separated by electrophoresis under denaturing conditions. Proteins were electrically transferred from the gel to a nitrocellulose membrane. Then the nitrocellulose membrane with immobilized proteins was washed with buffer I (20 mM Tris-HCl, pH 7.5; 150 mM NaCl; 0.05% twin-20) and incubated for 1 h in a 2% bovine serum albumin solution in buffer I. Then they were incubated for 16 h with primary antibodies to PD1 in 2% BSA in buffer I. After that, the membrane was washed with buffer I and incubated for 1 h with secondary antibodies conjugated with horseradish peroxidase (Manufacturer Bio-Rad) in a 1% milk solution in buffer I.

The membrane was washed with buffer I and stained using a commercial ECL™ chemiluminescence detection kit. Clones were selected that did not show specific bands corresponding to PD-1.

Generation of PD-1 Knockout NK-Cells and Antibiotic Resistance to Zeocin.

To increase the efficiency of the process of creating cells with a knockout PD-1 gene, a method for selecting NK-cells using a selective marker zeocin is proposed.

The process includes several steps:
1. Selection of a guide RNA sequence specific to the PD-1 gene having a sequence according to SEQ ID NO: 1;
2. Construction of an expression plasmid vector encoding the selected guide RNA and Cas9 endonuclease (pGR301);
3. Synthesis of a donor DNA fragment encoding an expression cassette for cell resistance to zeocin having the sequence according to SEQ ID NO: 9;
4. Transfection of a culture of NK-cells with a mixture of a plasmid vector and a fragment of donor DNA;
5. Cultivation of cells in a selective medium with zeocin.
6. Staining of surviving cells with anti PD-1 antibodies, and selection and cloning of cells with minimal signal using a flow sorter.
7. Culturing clones of cells, secondary selection of cells by immunoblotting with anti PD-1 antibodies.

For transfection of the cells, a mixture of the pGR301 vector and a pd1-Zeo DNA fragment, SEQ ID NO: 9, encoding the zeocin resistance gene was used. To synthesize a DNA fragment and pd1-Zeo polymerase chain reaction was used with overlapping primers. NK-cells were transfected with Lipofectamin 3000 (Thermo Fisher Scientific). For transfection with Lipofectamine 3000, cells were incubated in an RPMI medium with 20% fetal bovine serum until a cell density of 4 6×10$^5$ cells/ml was achieved. A mixture of Lipofectamine 3000 lipagent and DNA was prepared (at the ratio of 3 μL lipagent, 2 μg pGR301 vector, 2 μg pd1-Zeo DNA fragment, 8 μL P3000™ reagent, 100 μL Opti-MEM® Medium per 1 ml cell suspension). The mixture was incubated for 5 min and added to the cell suspension. The cells were incubated for 48 h at 37° C. and 5% CO2.

To select NK-cells with a knocked-out PD-1 gene using a selective marker zeocin 48 h after transfection, the cells were transferred to a selective medium (RPMI supplemented with zeocin) and cultured for 2-4 weeks. Surviving cells were stained with fluorescein-labeled anti-PD-1 antibodies. Samples of stained cells were separated using a cell sorter. Single cells with minimal or no fluorescent signal were selected in the wells of a 96-well plate with the RPMI medium with 20% fetal bovine serum. The cells were cultured for 2-4 weeks at 37° C. and 5% CO2 with replacement of the culture medium every 3-4 days.

The expression level of PD-1 in clones was assessed by immunoblotting with anti-PD-1 antibodies, similar to the protocol described for obtaining NK-cells with a knockout PD-1 gene.

Generation of NK-Cells with PD-1 Gene Knockout and Constitutive Increased Expression of Fas-Ligand.

To increase the activity of NK-cells, a method is proposed for producing NK-cells with a knockout PD-1 gene and constitutive increased expression of Fas-ligand.

The process includes several steps:
1. Selection of the guide RNA sequence specific to the PD-1 gene having the sequence according to SEQ ID NO: 1;
2. Construction of an expression plasmid vector encoding the selected guide RNA and Cas9 endonuclease (pGR301);
3. Synthesis of a donor DNA fragment encoding an expression cassette for Fas-ligand having the sequence according to SEQ ID NO: 16;
4. Transfection of a culture of NK-cells with a mixture of a plasmid vector and a fragment of donor DNA;
5. Cell staining with anti PD-1 antibodies and anti Fas-ligand antibodies. Selection and cloning of cells with minimal signal for PD-1 and maximal signal for Fas-ligand using a flow sorter.
6. Culturing cell clones, secondary cell selection by immunoblotting with anti PD-1 and anti Fas-ligand antibodies.

For transfection of cells, a mixture of the pGR301 vector and a pd1-FasL DNA fragment having the sequence according to SEQ ID NO: 16, encoding an expression cassette for expressing the Fas-ligand, was used. To synthesize a DNA fragment and pd1-FasL, a polymerase chain reaction with overlapping primers was used.

NK-cells were transfected with Lipofectamin 3000 (Thermo Fisher Scientific). For transfection with Lipofectamine 3000, cells were incubated in an RPMI medium with 20% fetal bovine serum until a cell density of 4-6×10$^5$ cells/ml was reached. A mixture of Lipofectamine 3000 lipagent and DNA was prepared (at a ratio of 3 μL lipagent, 2 μg pGR301 vector, 2 μg pd1-FasL DNA fragment, 8 μL P3000™ reagent, and 100 μL Opti-MEM® medium per 1 ml cell suspension). The mixture was incubated for 5 min and added to the cell suspension. The cells were incubated for 48 h at 37° C. and 5% CO2.

To select cells with a PD-1 knockout gene and constitutively increased expression of Fas-ligand, 48 h after transfection, cells were stained with a mixture of anti-PD-1 antibodies labeled with fluorescein and anti-Fas-ligand antibodies labeled with Alexa Fluor® 610-R-phycoerythrin. Cells with a minimum fluorescent signal of fluorescein and a maximum signal of Alexa Fluor® 610-R-phycoerythrin were selected and cloned.

To obtain labeled anti-Fas-ligand antibodies, we used monoclonal mouse anti-Fas-ligand antibodies (Manufacturer: BD Biosciences, clone G-247) and a Zenon™ Alexa Fluor™ 610-R-Phycoerythrin Mouse IgG1 Labeling Kit (Manufacturer: Invitrogen™, cat. no. Z25020).

The expression level of PD-1 in clones was assessed by immunoblotting with anti-PD-1 antibodies, similar to the protocol described for obtaining NK-cells with the knockout PD-1 gene. In clones with confirmed PD-1 knockout, the expression level of the Fas-ligand was assessed. Immunoblotting with anti-Fas-ligand antibodies (Manufacturer: BD Biosciences, clone G-247) was carried out in a manner similar to PD-1. As a result of the analysis, cells were selected in which the maximum signal of the bands corresponding to the Fas-ligand was detected.

Generation of PD-1 gene knockout NK-cells and constitutive increased TRAIL expression.

To increase the activity of NK-cells, a method is proposed for obtaining NK-cells with knockout PD-1 gene and constitutive increased TRAIL expression.

The process includes several steps:
1. Selection of a guide RNA sequence specific to the PD-1 gene having the sequence according to SEQ ID NO: 1;
2. Construction of an expression plasmid vector encoding the selected guide RNA and Cas9 endonuclease (pGR301);
3. Synthesis of a donor DNA fragment encoding an expression cassette for TRAIL having the sequence according to SEQ ID NO: 20;
4. Transfection of a culture of NK-cells with a mixture of a plasmid vector and a fragment of donor DNA;
5. Cell staining with anti-PD-1 antibodies and anti-TRAIL antibodies. Selection and cloning of cells with a minimum signal for PD-1 and a maximum signal for TRAIL using a flow sorter.
6. Cultivation of cell clones, secondary selection of cells by immunoblotting with anti PD-1 and anti TRAIL antibodies.

A mixture of the pGR301 vector and a pdl-TRAIL DNA fragment, SEQ ID NO: 20, encoding an expression cassette for TRAIL expression, was used to transfect the cells. To synthesize a DNA fragment and pdl-TRAIL, a polymerase chain reaction with overlapping primers was used. NK-cells were transfected using the Lipofectamin 3000 lipagent (Thermo Fisher Scientific). For transfection with Lipofectamine 3000, the cells were incubated in an RPMI medium with 20% fetal bovine serum until a cell density of 4-6×10$^5$ cells/ml was reached. A mixture of Lipofectamine 3000 lipagent and DNA was prepared at the ratio of 3 μL lipagent, 2 μg pGR301 vector, 2 μg a pdl-TRAIL DNA fragment, 8 μL P3000™ reagent, and 100 μL Opti-MEM® Medium medium per 1 ml cell suspension. The mixture was incubated for 5 min and added to the cell suspension. The cells were incubated for 48 h at 37° C. and 5% CO2.

To select cells with a knockout PD-1 gene and constitutively increased TRAIL expression, 48 h after transfection, the cells were stained with a mixture of anti-PD-1 antibodies labeled with fluorescein and anti-TRAIL antibodies labeled with Alexa Fluor® 610-R-phycoerythrin. Cells with a minimal fluorescent signal for fluorescein and a maximal signal for Alexa Fluor® 610-R-phycoerythrin were selected and cloned.

To obtain labeled anti-TRAIL antibodies, monoclonal mouse anti-TRAIL antibodies (Manufacturer: Abcam, clone 2E5, cat. ab2219) and a Zenon™ Alexa Fluor™ 610-R-Phycoerythrin Mouse IgG1 Labeling Kit (Manufacturer: Invitrogen™, cat. no. Z25020) were used.

The expression level of PD-1 in clones was assessed by immunoblotting with anti-PD-1 antibodies, similar to the protocol described for obtaining NK-cells with a knockout PD-1 gene. In clones with confirmed PD-1 knockout, the expression level of TRAIL was assessed. Immunoblotting was performed with anti-TRAIL antibodies (Manufacturer: Abcam, clone 75411.11, cat. no. ab10516) using a method similar to PD-1. As a result of the analysis, cells were selected in which the maximum signal of the bands corresponding to TRAIL was detected.

The cell lines HeLa (human cervical adenocarcinoma), K562 (human myeloid leukemia), A172 (human glioblastoma), and T98G (human glioblastoma) were obtained from the Russian collection of vertebrate cell cultures of the Institute of Cytology, Russian Academy of Sciences (St. Petersburg).

The possibility of using the invention is illustrated by examples confirming the cytotoxic activity of NK92-PD1 and NK92-PD1-TRAIL cells to induce apoptosis or lysis of various types of mammalian cancer cells.

Example 1. Evaluation of the Cytotoxic Activity of NK92 and NK92-PD1 Cells Incubated with Target Cells K562 (Human Myeloid Leukemia), and With Target Cells HeLa (Adenocarcinoma of the Human Cervix)

In the wells of a 96-well plate, 100 μL of a suspension of HeLa or K562 cells ($2*10^4$/well) in DMEM (Gibco) or RPMI 1640 (Gibco) media containing 10% fetal calf serum (Hyclone), respectively, were added and incubated for 16 h at 37° C. and 5% CO2. Then, 50 μL of a suspension of NK92 and NK92-PD1 cells ($6*10^4$/well) in αMEM medium supplemented with 2 mM L-glutamine, sodium bicarbonate (1.5 g/L), 0.2 mM inositol, 0.1 mM 2-mercaptoethanol, 0.02 mM folic acid, 250 U/ml recombinant interleukin 2 (Prospec), and 25% fetal calf serum (Hyclone) were added to the wells with cells. The cells were incubated for 6 hours at 37° C. and 5% CO2 and visualized with a microscope in transmitted light (see FIG. 5 and FIG. 6). Wells with HeLa cells were washed with buffered saline, the remaining cells were stained with 0.2% neutral red solution and evaluated for light absorption (wavelength-540 nm) using a plate photometer. The percentage of surviving cells was determined as the ratio of the optical density of the experimental wells with HeLa cells with NK92 or NK92-PD1 cells, and the optical density of the control wells with HeLa cells. The result of evaluating the cytotoxic activity of NK92 and NK92-PD1-TRAIL cells incubated with HeLa target cells is shown in FIG. 7.

Example 2. Comparative Growth Kinetics of the NK92 and NK92-PD1 Cultures

To assess proliferative activity, 100 μL of a suspension of NK92 or NK92-PD1 cells ($1*10^4$/well) in an αMEM medium supplemented with 2 mM L-glutamine, sodium bicarbonate (1.5 g/L), 0.2 mM inositol, 0.1 mM 2-mercaptoethanol, 0.02 mM folic acid, 400 U/ml recombinant interleukin 2 (Prospec), and 25% fetal bovine serum (Hyclone) were added to the wells of a 96-ell plate and incubated for 72 h at 37° C. and 5% CO2. Every 24 h, aliquots of cells were taken from 5 wells for each type of cells, an equal volume of a 0.4% trypan blue solution was added to them, and the number of living cells was counted using a Goryaev camera. The result of evaluating the growth kinetics of NK92 and NK92-PD1 cultures is shown in FIG. 8.

Example 3. Assessment of the Cytotoxic Activity of NK92 and NK92-PD1-TRAIL Cells on A 172 Cells (Human Glioblastoma)

In the wells of a 96-well plate, 100 μL of a suspension of A172 cells ($2*10^4$/well) in an αMEM medium supplemented with 10% fetal bovine serum (Hyclone) was added and incubated for 16 h at 37° C. and 5% CO2. Then, 50 μL of a suspension of NK92 and NK92-PD1-TRAIL cells ($6*10^4$/well) was placed in an αMEM medium supplemented with 2 mM L-glutamine, sodium bicarbonate (1.5 g/L), 0.2 mM inositol, 0.1 mM 2-mercaptoethanol, 0.02 mM folic acid, 250 U/ml recombinant interleukin 2 (Prospec), and 25% fetal calf serum (Hyclone). The cells were incubated for 6 h at 37° C. and 5% CO2 and visualized with a microscope in transmitted light. Wells with A172 cells were washed with buffered saline, the remaining cells were stained with a 0.2% solution of neutral red and evaluated for light absorption (wavelength-540 nm) using a plate photometer. The percentage of surviving A172 cells was determined as the ratio of the optical density of the experimental wells (A172 with NK92 or NK92-PD1 PD1-TRAIL) and the optical density of the control wells with A172 cells. The result of evaluating the cytotoxic activity of NK92 and NK92-PD1-TRAIL cells incubated with target A172 cells is shown in FIG. 9.

Example 4. Evaluation of the Cytotoxic Activity of NK92 and NK92-PD1-TRAIL Cells on T98G Cells (Human Glioblastoma)

100 μL of a suspension of T98G cells ($2*10^4$/l) in αMEM medium supplemented with 10% fetal bovine serum (Hyclone) was added to the wells of a 96-well plate and incubated for 16 h at 37° C. and 5% CO2. Then, 50 μL of a suspension of NK92 and NK92-PD1-TRAIL cells ($6*10^4$/well) in αMEM medium supplemented with 2 mM L-glutamine, sodium bicarbonate (1.5 g/L), 0.2 mM inositol, 0.1 mM 2-mercaptoethanol, 0.02 mM folic acid, 250 U/ml recombinant interleukin 2 (Prospec), and 25% fetal calf serum (Hyclone). The cells were incubated for 8 h at 37° C. and 5% CO2 and visualized with a microscope in transmitted light. Wells with T98G cells were washed with buffered saline, the remaining cells were stained with 0.2% neutral red solution and evaluated for light absorption (wavelength-540 nm) using a plate photometer. The percentage of surviving cells was determined as the ratio of the optical density of the experimental wells (T98G with NK92 or NK92-PD1 PD1-TRAIL) and the optical density of the control wells (T98G cells). The result of evaluating the cytotoxic activity of NK92 and NK92-PD1-TRAIL cells incubated with T98G target cells is shown in FIG. 10.

INDUSTRIAL APPLICABILITY

In accordance with the object of the invention, modified NK-cells, NK-cell lines, or compositions thereof with increased cytotoxicity are intended for use in the treatment of cancer in a patient. In preferred embodiments of the invention, the modified NK-cell, NK-cell line, or a composition thereof is intended for use in the treatment of blood cancer, including acute lymphoblastic leukemia (ALL), acute myeloid leukemia (AML), chronic lymphocytic leukemia (CLL), and chronic myeloid leukemia (CML). A modified NK-cell and an NK-cell line can be used to treat: Hodgkin's lymphomas and non-Hodgkin's lymphomas, including T-cell lymphomas, B-cell lymphomas, asymptomatic myelomas, smoldering multiple myelomas (SMM), active myelomas, or myeloma light chains.

INFORMATION SOURCES

1. HONJO T., SHIBAYAMA S. SUBSTANCE SPECIFIC TO HUMAN PD-1. Japanese Patent LUR6157574 (B2) (Jul. 5, 2017).
2. JOHNSON BRYON D., MILLMAN R. METHODS FOR TREATING HEMATOLOGIC CANCERS. Application USA No. US2016222121A1 (Aug. 4, 2016).
3. LIZONGHAI P. CHIMERIC ANTIGEN RECEPTOR-MODIFIED IMMUNE EFFECTOR CELL CARRYING PD-L1 BLOCKING AGENT. European Patent No. EP3382009 (Oct. 3, 2018).
4. Djoke Hendriks et al. Programmed Death Ligand 1 (PD-L1)-targeted TRAIL combines PD-L1-mediated checkpoint inhibition with TRAIL-mediated apoptosis induction. Oncoimmunology. 2016 August; 5(8).
5. Modiano J F1, Bellgrau D. Fas ligand-based immunotherapy: A potent and effective neoadjuvant with checkpoint inhibitor properties, or a systemically toxic promoter of tumor growth? Discov Med. 2016 February; 21(114):109-16.
6. HU BIAN; HUANG XINGXU Method for human PD1 gene specific knockout through CRISPR-Cas9 (clustered regularly interspaced short palindromic repeat) and sgRNA (single guide RNA) for specially targeting PD1 gene. Chinese patent CN103820454 (May 28, 2014).
7. Su S et al. CRISPR-Cas9 mediated efficient PD-1 disruption on human primary T cells from cancer patients. Sci Rep. 2016 Jan. 28.
8. Xiuyan Wang, Isabelle Riviere: Clinical manufacturing of CART cells: foundation of a promising therapy. Oncolytics 2016.
9. Galat V, Galat Y, Perepitchka M, et al. Transgene reactivation in induced pluripotent stem cell derivatives and reversion to pluripotency of induced pluripotent stem cell-derived mesenchymal stem cells. Stem Cells Dev. 2016; 25:1060-72.
10. Galat, Y., Dambaeva, S., Elcheva, I., Khanolkar, A., Beaman, K., Iannaccone, P. M., Galat, V., Cytokine-free directed differentiation of human pluripotent stem cells efficiently produces hemogenic endothelium with lymphoid potential. Stem Cell Res Ther 8, 67 (2017).
11. Kaufman; Dan S. Knorr; David A. Method for developing natural killer cells from stem cells. U.S. Pat. No. 9,260,696 (Feb. 16, 2016).
12. O'Dwyer M. Modified natural killer cells and natural killer cell lines having increased cytotoxicity. U.S. Pat. No. 10,034,925 (Jul. 31, 2018).

SEQUENCE LISTING

```
<160> NUMBER OF SEQ ID NOS: 21

<210> SEQ ID NO 1
<211> LENGTH: 96
<212> TYPE: DNA
<213> ORGANISM: Artificial Sequence
<220> FEATURE:
<223> OTHER INFORMATION: Synthetic oligonucleotide, Guide RNA sequence
      specific to the PD-1 gene

<400> SEQUENCE: 1
gtctgggcgg tgctacaact gttttagagc tagaaatagc aagttaaaat aaggctagtc    60
cgttatcaac ttgaaaaagt ggcaccgagt cggtgc                              96

<210> SEQ ID NO 2
<211> LENGTH: 96
<212> TYPE: DNA
<213> ORGANISM: Artificial Sequence
<220> FEATURE:
<223> OTHER INFORMATION: Synthetic oligonucleotide, Guide RNA sequence
      specific to the PD-1 gene

<400> SEQUENCE: 2
gggcggtgct acaactgggc gttttagagc tagaaatagc aagttaaaat aaggctagtc    60
cgttatcaac ttgaaaaagt ggcaccgagt cggtgc                              96

<210> SEQ ID NO 3
<211> LENGTH: 96
<212> TYPE: DNA
<213> ORGANISM: Artificial Sequence
<220> FEATURE:
<223> OTHER INFORMATION: Synthetic oligonucleotide, Guide RNA sequence
      specific to the PD-1 gene
```

<400> SEQUENCE: 3
ggcgccctgg ccagtcgtct gttttagagc tagaaatagc aagttaaaat aaggctagtc      60
cgttatcaac ttgaaaaagt ggcaccgagt cggtgc                                96

<210> SEQ ID NO 4
<211> LENGTH: 96
<212> TYPE: DNA
<213> ORGANISM: Artificial Sequence
<220> FEATURE:
<223> OTHER INFORMATION: Synthetic oligonucleotide, Guide RNA sequence
      specific to the PD-1 gene

<400> SEQUENCE: 4
gccctggcca gtcgtctggg gttttagagc tagaaatagc aagttaaaat aaggctagtc      60
cgttatcaac ttgaaaaagt ggcaccgagt cggtgc                                96

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide, Target DNA sequence
      for vector pGR301

<400> SEQUENCE: 5
gtctgggcgg tgctacaact ggg                                              23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide, Target DNA sequence
      for vector pGR302

<400> SEQUENCE: 6
gggcggtgct acaactgggc tgg                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide, Target DNA sequence
      for vector pGR303

<400> SEQUENCE: 7
ggcgccctgg ccagtcgtct ggg                                              23

<210> SEQ ID NO 8
<211> LENGTH: 23
<212> TYPE: DNA
<213> ORGANISM: Artificial Sequence
<220> FEATURE:
<223> OTHER INFORMATION: Target DNA sequence for vector pGR304

<400> SEQUENCE: 8
gccctggcca gtcgtctggg cgg                                              23

<210> SEQ ID NO 9
<211> LENGTH: 2371
<212> TYPE: DNA
<213> ORGANISM: Artificial Sequence
<220> FEATURE:

<223> OTHER INFORMATION: Synthetic polynucleotide, Donor DNA fragment
      encoding an expression cassette for cell resistance to zeocin

<400> SEQUENCE: 9

```
tgagcagaga cacagaggag aagggggccc tgagctgggg agacccccac ggggtagggc      60
gtggggggcca cgggcccacc tcctccccat ctcctctgtc tccctgtctc tgtctctctc     120
tccctccccc accctctccc cagtcctacc ccctcctcac ccctcctccc ccagcactgc     180
ctctgtcact ctcgcccacg tggatgtgga ggaagagggg gcgggagcaa ggggcgggca     240
ccctcccttc aacctgacct gggacagttt cccttccgct cacctccgcc tgagcagtgg     300
agaaggcggc actctggtgg ggctgctcca ggcatgcaga tcccacaggc gccctggcca     360
gtcgtctggg cggtgctacc cggtaacctg caggcgttac ataacttacg gtaaatggcc     420
cgcctggctg accgcccaac gacccccgcc cattgacgtc aataatgacg tatgttccca     480
tagtaacgcc aatagggact tccattgacg tcaatgggt ggagtattta cggtaaactg     540
cccacttggc agtacatcaa gtgtatcata tgccaagtac gccccctatt gacgtcaatg     600
acggtaaatg gcccgcctgg cattatgccc agtacatgac cttatgggac tttcctactt     660
ggcagtacat ctacgtatta gtcatcgcta ttaccatgat gatgcggttt tggcagtaca     720
tcaatgggcg tggatagcgg tttgactcac ggggatttcc aagtctccac cccattgacg     780
tcaatgggag tttgttttga ctagtcaggg ccccaacccc cccaagcccc catttcacaa     840
cacgctggcg ctacaggcgc gtgacttccc cttgctttgg ggcgggggc tgagactcct     900
atgtgctccg gattggtcag gcacggcctt cggccccgcc tcctgccacc gcagattggc     960
cgctaggcct ccccgagcgc cctgcctccg agggccggcg caccataaaa gaagccgccc    1020
tagccacgtc ccctcgcagt tcggcggtcc cgcgggtctg tctcaagctt ctgccttctc    1080
cctcctgtga gtttggtaag tcactgactg tctatgcctg ggaaagggtg ggcaggagat    1140
ggggcagtgc aggaaaagtg gcactatgaa ccctgcagcc ctagtttgac aattaatcat    1200
tggcatagta tatctgcata gtataataca actcactata gcaattgtac taaccttctt    1260
ctctttcctc tcctgacagg aggagccatc atggccaagt tgaccagtgc cgttccggtg    1320
ctcaccgcgc gcgacgtcgc cggagcggtc gagttctgga ccgaccggct cgggttctcc    1380
cgggacttcg tggaggacga cttcgccggt gtggtccggg acgacgtgac cctgttcatc    1440
agcgcggtcc aggaccaggt ggtgccggac aacaccctgg cctgggtgtg ggtgcgcggc    1500
ctggacgagc tgtacgccga gtggtcggag gtcgtgtcca cgaacttccg gacgcctcc    1560
gggccggcca tgaccgagat cggcgagcag ccgtggggc gggagttcgc cctgcgcgac    1620
ccggccggca actgcgtgca ctttgtggca gaggagcagg actgaggata agctagaagc    1680
tcgctttctt gctgtccaat ttctattaaa ggttcctttg ttccctaagt ccaactacta    1740
aactggggga tattatgaag ggccttgagc atctggattc tgcctaataa aaaacattta    1800
ttttcattgc aatgatgtat ttaaattatt tctgaatatt ttactaaaaa gggaatgtgg    1860
gaggtcagtg catttaaaac ataaagaaat gaagagctag ttcaaacctt gggaaaatac    1920
actatatctt aaactccatg aaagaaggtg aggctgcaaa cagctaatgc acattggcaa    1980
cagcccctga tgcctatgcc ttattcatcc ctcagaaaag gattcaagta gaggcttgat    2040
ttggaggtta agttttgct atgctgtatt ttagaattaa ttccatacca ctctagctgg    2100
cggccaggat ggttcttagg taggtggggt cggcggtcag gtgtcccaga gccagggtc    2160
tggagggacc ttccacccctc agtccctggc aggtcggggg gtgctgaggc gggcctggcc    2220
```

```
ctggcagccc agggtcccg gagcgagggg tctggaggga cctttcactc tcagtccctg      2280
gcaggtcggg gggtgctgtg gcaggcccag ccttggcccc cagctctgcc ccttaccctg      2340
agctgtgtgg ctttgggcag ctcgaactcc t                                    2371

<210> SEQ ID NO 10
<211> LENGTH: 379
<212> TYPE: DNA
<213> ORGANISM: Artificial Sequence
<220> FEATURE:
<223> OTHER INFORMATION: Synthetic polynucleotide, A fragment containing
      the sequence of the first part of the pd1 gene with a size of 379
      base pairs

<400> SEQUENCE: 10
tgagcagaga cacagaggag gaagggggccc tgagctgggg agaccccac ggggtagggc       60 gtgggggcca cgggcccacc tcctccccat ctcctctgtc tccctgtctc tgtctctctc      120 tccctcccccc accctctccc cagtcctacc ccctcctcac ccctcctccc ccagcactgc    180
ctctgtcact ctcgcccacg tggatgtgga ggaagagggg gcgggagcaa gggggcgggca    240 ccctcccttc aacctgacct gggacagttt ccttccgct cacctccgcc tgagcagtgg      300
agaaggcggc actctggtgg ggctgctcca ggcatgcaga tcccacaggc gccctggcca    360
gtcgtctggg cggtgctac                                                  379

<210> SEQ ID NO 11
<211> LENGTH: 405
<212> TYPE: DNA
<213> ORGANISM: Artificial Sequence
<220> FEATURE:
<223> OTHER INFORMATION: Synthetic polynucleotide, A fragment containing
      the sequence of CMV enhancer with a size of 405 base pairs

<400> SEQUENCE: 11
cgttacataa cttacggtaa atggcccgcc tggctgaccg cccaacgacc cccgcccatt       60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta    240
catgacctta tgggactttc ctacttggca gtacatctac gtattagtca tcgctattac    300
catgatgatg cggttttggc agtacatcaa tgggcgtgga tagcggtttg actcacgggg    360
atttccaagt ctccacccca ttgacgtcaa tgggagtttg ttttg                    405

<210> SEQ ID NO 12
<211> LENGTH: 263
<212> TYPE: DNA
<213> ORGANISM: Artificial Sequence
<220> FEATURE:
<223> OTHER INFORMATION: Synthetic polynucleotide, A fragment containing
      the sequence-hFerL Promoter with a size of 263 base pairs

<400> SEQUENCE: 12
cagggcccca acccccccaa gccccccattt cacaacacgc tggcgctaca ggcgcgtgac      60
ttccccttgc tttggggcgg ggggctgaga ctcctatgtg ctccggattg gtcaggcacg    120
gccttcggcc ccgcctcctg ccaccgcaga ttggccgcta ggcctccccg agcgccctgc    180
ctccgagggc cggcgcacca taaagaagc cgccctagcc acgtcccctc gcagttcggc     240
ggtcccgcgg gtctgtctca agc                                            263
```

<210> SEQ ID NO 13
<211> LENGTH: 375
<212> TYPE: DNA
<213> ORGANISM: Artificial Sequence
<220> FEATURE:
<223> OTHER INFORMATION: Synthetic polynucleotide, A fragment containing the sequence-Zeo-zeocin resistance gene with a size of 375 base pairs

<400> SEQUENCE: 13

```
atggccaagt tgaccagtgc cgttccggtg ctcaccgcgc gcgacgtcgc cggagcggtc        60
gagttctgga ccgaccggct cgggttctcc cgggacttcg tggaggacga cttcgccggt       120
gtggtccggg acgacgtgac cctgttcatc agcgcggtcc aggaccaggt ggtgccggac       180
aacaccctgg cctgggtgtg ggtgcgcggc ctggacgagc tgtacgccga gtggtcggag       240
gtcgtgtcca cgaacttccg ggacgcctcc gggccggcca tgaccgagat cggcgagcag       300
ccgtgggggc gggagttcgc cctgcgcgac ccggccggca actgcgtgca ctttgtggca       360
gaggagcagg actga                                                         375
```

<210> SEQ ID NO 14
<211> LENGTH: 401
<212> TYPE: DNA
<213> ORGANISM: Artificial Sequence
<220> FEATURE:
<223> OTHER INFORMATION: Synthetic polynucleotide, A fragment containing the sequence beta-Glo polyA Signal with a size of 401 base pairs

<400> SEQUENCE: 14

```
ctagaagctc gctttcttgc tgtccaattt ctattaaagg ttcctttgtt ccctaagtcc        60
aactactaaa ctgggggata ttatgaaggg ccttgagcat ctggattctg cctaataaaa       120
aacatttatt ttcattgcaa tgatgtattt aaattatttc tgaatatttt actaaaaagg       180
gaatgtggga ggtcagtgca tttaaaacat aaagaaatga agagctagtt caaaccttgg       240
gaaaatacac tatatcttaa actccatgaa agaaggtgag gctgcaaaca gctaatgcac       300
attggcaaca gccccctgatg cctatgcctt attcatccct cagaaaagga ttcaagtaga       360
ggcttgattt ggaggttaaa gttttgctat gctgtatttt a                            401
```

<210> SEQ ID NO 15
<211> LENGTH: 276
<212> TYPE: DNA
<213> ORGANISM: Artificial Sequence
<220> FEATURE:
<223> OTHER INFORMATION: Synthetic polynucleotide, A fragment containing the sequence of the second part of the pd1 gene with a size of 276 base pairs

<400> SEQUENCE: 15

```
gctggcggcc aggatggttc ttaggtaggt ggggtcggcg gtcaggtgtc ccagagccag        60
gggtctggag ggaccttcca ccctcagtcc ctggcaggtc gggggtgct gaggcgggcc       120 tggccctggc agcccagggg tcccggagcg aggggtctgg agggaccttt cactctcagt       180
ccctggcagg tcggggggtg ctgtggcagg cccagccttg cccccagct ctgcccctta       240 ccctgagctg tgtggctttg ggcagctcga actcct                                  276
```

<210> SEQ ID NO 16
<211> LENGTH: 2473
<212> TYPE: DNA
<213> ORGANISM: Artificial Sequence
<220> FEATURE:

<223> OTHER INFORMATION: Synthetic polynucleotide, A fragment of donor
      DNA is synthesized encoding an expression cassette for the Fas-
      ligand

<400> SEQUENCE: 16

| | | | | | |
|---|---|---|---|---|---|
| tgagcagaga | cacagaggag | gaaggggccc | tgagctgggg | agacccccac | ggggtagggc | 60 |
| gtggggggcca | cgggcccacc | tcctccccat | ctcctctgtc | tccctgtctc | tgtctctctc | 120 |
| tccctccccc | accctctccc | cagtcctacc | ccctcctcac | ccctcctccc | ccagcactgc | 180 |
| ctctgtcact | ctcgcccacg | tggatgtgga | ggaagagggg | gcgggagcaa | ggggcgggca | 240 |
| ccctccctttc | aacctgacct | gggacagttt | cccttccgct | cacctccgcc | tgagcagtgg | 300 |
| agaaggcggc | actctggtgg | ggctgctcca | ggcatgcaga | tcccacaggc | gccctggcca | 360 |
| gtcgtctggg | cggtgctacc | cggtacgcgt | tgacattgat | tattgactag | ttattaatag | 420 |
| taatcaatta | cggggtcatt | agttcatagc | ccatatatgg | agttccgcgt | tacataactt | 480 |
| acggtaaatg | gcccgcctgg | ctgaccgccc | aacgacccc | gcccattgac | gtcaataatg | 540 |
| acgtatgttc | ccatagtaac | gccaataggg | actttccatt | gacgtcaatg | ggtggactat | 600 |
| ttacggtaaa | ctgcccactt | ggcagtacat | caagtgtatc | atatgccaag | tacgccccct | 660 |
| attgacgtca | atgacggtaa | atggcccgcc | tggcattatg | cccagtacat | gaccttatgg | 720 |
| gactttccta | cttggcagta | catctacgta | ttagtcatcg | ctattaccat | ggtgatgcgg | 780 |
| ttttggcagt | acatcaatgg | gcgtggatag | cggtttgact | cacggggatt | tccaagtctc | 840 |
| caccccattg | acgtcaatgg | gagtttgttt | tggcaccaaa | atcaacggga | ctttccaaaa | 900 |
| tgtcgtaaca | actccgcccc | attgacgcaa | atgggcggta | ggcgtgtacg | gtgggaggtc | 960 |
| tatataagca | gagctctctg | gctaactaga | gaacccactg | cttactggct | tatcgaaatt | 1020 |
| aatacgactc | actatagggga | gacccaagct | tatgcagcag | cccttcaatt | acccatatcc | 1080 |
| ccagatctac | tgggtggaca | gcagtgccag | ctctccctgg | gcccctccag | gcacagttct | 1140 |
| tccctgtcca | acctctgtgc | ccagaaggcc | tggtcaaagg | aggccaccac | caccaccgcc | 1200 |
| accgccacca | ctaccacctc | cgccgccgcc | gccaccactg | cctccactac | cgctgccacc | 1260 |
| cctgaagaag | agagggaacc | acagcacagg | cctgtgtctc | cttgtgatgt | ttttcatggt | 1320 |
| tctggttgcc | ttggtaggat | tgggcctggg | gatgtttcag | ctcttccacc | tacagaagga | 1380 |
| gctggcagaa | ctccgagagt | ctaccagcca | gatgcacaca | gcatcatctt | tggagaagca | 1440 |
| aataggccac | cccagtccac | cccctgaaaa | aaaggagctg | aggaaagtgg | cccatttaac | 1500 |
| aggcaagtcc | aactcaaggt | ccatgcctct | ggaatgggaa | gacacctatg | gaattgtcct | 1560 |
| gctttctgga | gtgaagtata | agaagggtgg | ccttgtgatc | aatgaaactg | gctgtacttt | 1620 |
| tgtatattcc | aaagtatact | tccggggtca | atcttgcaac | aacctgcccc | tgagccacaa | 1680 |
| ggtctacatg | aggaactcta | agtatcccca | ggatctggtg | atgatggagg | ggaagatgat | 1740 |
| gagctactgc | actactgggc | agatgtgggc | ccgcagcagc | tacctggggg | cagtgttcaa | 1800 |
| tcttaccagt | gctgatcatt | tatatgtcaa | cgtatctgag | ctctctctgg | tcaattttga | 1860 |
| ggaatctcag | acgttttttcg | gcttatataa | gctctaactc | gagcatgcat | ctagagggcc | 1920 |
| ctattctata | gtgtcaccta | aatgctagag | ctcgctgatc | agcctcgact | gtgccttcta | 1980 |
| gttgccagcc | atctgttgtt | tgcccctccc | ccgtgccttc | cttgaccctg | gaaggtgcca | 2040 |
| ctcccactgt | cctttcctaa | taaaatgagg | aaattgcatc | gcattgtctg | agtaggtgtc | 2100 |
| attctattct | ggggggtggg | gtggggcagg | acagcaaggg | ggaggattgg | gaagacaata | 2160 |
| gcaggcatgc | tggggatgcg | gtgggctcta | tggcctagct | ggcggccagg | atggttctta | 2220 |

```
ggtaggtggg gtcggcggtc aggtgtccca gagccagggg tctggaggga ccttccaccc    2280
tcagtccctg gcaggtcggg gggtgctgag gcgggcctgg ccctggcagc ccaggggtcc    2340
cggagcgagg ggtctggagg gacctttcac tctcagtccc tggcaggtcg ggggtgctg    2400 tggcaggccc agccttggcc cccagctctg ccccttaccc tgagctgtgt ggctttgggc    2460
agctcgaact cct                                                       2473
```

<210> SEQ ID NO 17
<211> LENGTH: 588
<212> TYPE: DNA
<213> ORGANISM: Artificial Sequence
<220> FEATURE:
<223> OTHER INFORMATION: Synthetic polynucleotide, A fragment containing
      the sequence CMV Promoter with a size of 588 base pairs

<400> SEQUENCE: 17

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctc                 588
```

<210> SEQ ID NO 18
<211> LENGTH: 846
<212> TYPE: DNA
<213> ORGANISM: Artificial Sequence
<220> FEATURE:
<223> OTHER INFORMATION: Synthetic polynucleotide, A fragment containing
      the sequence Fas-ligand with a size of 846 base pairs

<400> SEQUENCE: 18

```
atgcagcagc ccttcaatta cccatatccc cagatctact gggtggacag cagtgccagc     60
tctccctggg cccctccagg cacagttctt ccctgtccaa cctctgtgcc cagaaggcct    120
ggtcaaagga ggccaccacc accaccgcca ccgccaccac taccacctcc gccgccgccg    180
ccaccactgc ctccactacc gctgccaccc ctgaagaaga gagggaacca cagcacaggc    240
ctgtgtctcc ttgtgatgtt tttcatggtt ctggttgcct tggtaggatt gggcctgggg    300
atgtttcagc tcttccacct acagaaggag ctggcagaac tccgagagtc taccagccag    360
atgcacacag catcatcttt ggagaagcaa ataggccacc ccagtccacc ccctgaaaaa    420
aaggagctga ggaaagtggc ccatttaaca ggcaagtcca actcaaggtc catgcctctg    480
gaatgggaag acacctatgg aattgtcctg ctttctggag tgaagtataa aaagggtggc    540
cttgtgatca tgaaactggg ctgtactttg gtatattcca agtatacttc cggggtcaa    600 tcttgcaaca acctgcccct gagccacaag gtctacatga gaactctaa gtatcccag    660 gatctggtga tgatggaggg gaagatgatg agctactgca ctactgggca gatgtgggcc    720
```

```
cgcagcagct acctgggggc agtgttcaat cttaccagtg ctgatcattt atatgtcaac    780
gtatctgagc tctctctggt caattttgag gaatctcaga cgttttcgg cttatataag     840 ctctaa                                                               846
```

<210> SEQ ID NO 19
<211> LENGTH: 225
<212> TYPE: DNA
<213> ORGANISM: Artificial Sequence
<220> FEATURE:
<223> OTHER INFORMATION: Synthetic polynucleotide, A fragment containing
      the sequence BGH polyA Signal with a size of 225 base pairs

<400> SEQUENCE: 19

```
ctgtgccttc tagttgccag ccatctgttg tttgcccctc ccccgtgcct tccttgaccc    60
tggaaggtgc cactcccact gtcctttcct aataaaatga ggaaattgca tcgcattgtc   120
tgagtaggtg tcattctatt ctggggggtg ggtggggca ggacagcaag ggggaggatt    180
gggaagacaa tagcaggcat gctggggatg cggtgggctc tatgg                   225
```

<210> SEQ ID NO 20
<211> LENGTH: 2473
<212> TYPE: DNA
<213> ORGANISM: Artificial Sequence
<220> FEATURE:
<223> OTHER INFORMATION: Synthetic polynucleotide, A fragment of donor
      DNA is synthesized encoding an expression cassette for TRAIL

<400> SEQUENCE: 20

```
tgagcagaga cacagaggag aaggggccc tgagctgggg agacccccac ggggtagggc      60
gtggggccca cggcccacc tcctccccat ctcctctgtc tcctgtctc tgtctctctc     120 tccctccccc accctctccc cagtcctacc ccctcctcac ccctcctccc ccagcactgc   180
ctctgtcact ctcgcccacg tggatgtgga ggaagagggg gcgggagcaa ggggcgggca   240
ccctcccttc aacctgacct gggacagttt ccctccgct cacctccgcc tgagcagtgg    300
agaaggcggc actctggtgg ggctgctcca ggcatgcaga tcccacaggc gccctggcca   360
gtcgtctggg cggtgctacc cggtacgcgt tgacattgat tattgactag ttattaatag   420
taatcaatta cggggtcatt agttcatagc ccatatatgg agttccgcgt tacataactt   480
acggtaaatg gcccgcctgg ctgaccgccc aacgaccccc gcccattgac gtcaataatg   540
acgtatgttc ccatagtaac gccaataggg actttccatt gacgtcaatg ggtggactat   600
ttacggtaaa ctgcccactt ggcagtacat caagtgtatc atatgccaag tacgccccct   660
attgacgtca atgacggtaa atggcccgcc tggcattatg cccagtacat gaccttatgg   720
gactttccta cttggcagta catctacgta ttagtcatcg ctattaccat ggtgatgcgg   780
ttttggcagt acatcaatgg gcgtggatag cggtttgact cacggggatt tccaagtctc   840 cacccccattg acgtcaatgg gagtttgttt tggcaccaaa atcaacggga ctttccaaaa   900
tgtcgtaaca actccgcccc attgacgcaa atgggcggta ggcgtgtacg gtgggaggtc   960
tatataagca gagctctctg gctaactaga gaacccactg cttactggct tatcgaaatt  1020
aatacgactc actataggga gacccaagct tatggctatg atgaggtcc agggggggacc  1080 cagcctggga cagacctgcg tgctgatcgt gatcttcaca gtgctcctgc agtctctctg  1140
tgtggctgta acttacgtgt actttaccaa cgagctgaag cagatgcagg acaagtactc  1200
caaaagtggc attgcttgtt tcttaaaaga agatgacagt tattgggacc ccaatgacga  1260
```

```
agagagtatg aacagcccct gctggcaagt caagtggcaa ctccgtcagc tcgttagaaa   1320
gatgattttg agaacctctg aggaaaccat ttctacagtt caagaaaagc aacaaaatat   1380 ttctcccta gtgagagaaa gaggtcctca gagagtagca gctcacataa ctgggaccag    1440
aggaagaagc aacacattgt cttctccaaa ctccaagaat gaaaaggctc tgggccgcaa   1500
aataaactcc tgggaatcat caaggagtgg gcattcattc ctgagcaact tgcacttgag   1560
gaatggtgaa ctggtcatcc atgaaaaagg gttttactac atctattccc aaacatactt   1620
tcgatttcag gaggaaataa agaaaacac aaagaacgac aaacaaatgg tccaatatat    1680
ttacaaatac acaagttatc ctgaccctat attgttgatg aaaagtgcta gaaatagttg    1740
ttggtctaaa gatgcagaat atggactcta ttccatctat caaggggaa tatttgagct     1800 taaggaaaat gacagaattt ttgtttctgt aacaaatgag cacttgatag acatggacca   1860
tgaagccagt ttttcgggg cctttttagt tggctaactc gagcatgcat ctagagggcc     1920
ctattctata gtgtcaccta aatgctagag ctcgctgatc agcctcgact gtgccttcta   1980
gttgccagcc atctgttgtt tgcccctccc ccgtgccttc cttgaccctg gaaggtgcca   2040
ctcccactgt cctttcctaa taaaatgagg aaattgcatc gcattgtctg agtaggtgtc   2100
attctattct ggggggtggg gtggggcagg acagcaaggg ggaggattgg gaagacaata   2160
gcaggcatgc tggggatgcg gtgggctcta tggcctagct ggcggccagg atggttctta   2220
ggtaggtggg gtcggcggtc aggtgtccca gagccagggg tctggaggga ccttccaccc   2280
tcagtccctg gcaggtcggg gggtgctgag gcgggcctgg ccctggcagc caggggtcc    2340 cggagcgagg ggtctggagg gacctttcac tctcagtccc tggcaggtcg ggggtgctg    2400 tggcaggccc agccttggcc cccagctctg ccccttaccc tgagctgtgt ggctttgggc   2460
agctcgaact cct                                                      2473
```

<210> SEQ ID NO 21
<211> LENGTH: 846
<212> TYPE: DNA
<213> ORGANISM: Artificial Sequence
<220> FEATURE:
<223> OTHER INFORMATION: Synthetic polynucleotide, A fragment containing
      the sequence TRAIL with a size of 846 base pairs

<400> SEQUENCE: 21

```
atggctatga tggaggtcca ggggggaccc agcctgggac agacctgcgt gctgatcgtg     60
atcttcacag tgctcctgca gtctctctgt gtggctgtaa cttacgtgta ctttaccaac    120
gagctgaagc agatgcagga caagtactcc aaaagtggca ttgcttgttt cttaaaagaa    180
gatgacagtt attgggaccc caatgacgaa gagagtatga acagcccctg ctggcaagtc    240
aagtggcaac tccgtcagct cgttagaaag atgattttga gaacctctga ggaaaccatt    300
tctacagttc aagaaaagca acaaaatatt ctccctag tgagagaaag aggtcctcag      360
agagtagcag ctcacataac tgggaccaga ggaagaagca acacattgtc ttctccaaac    420
tccaagaatg aaaaggctct gggccgcaaa ataaactcct gggaatcatc aaggagtggg    480
cattcattcc tgagcaactt gcacttgagg aatggtgaac tggtcatcca tgaaaaaggg    540
ttttactaca tctattccca aacatacttt cgatttcagg aggaaataaa agaaaacaca    600
aagaacgaca aacaaatggt ccaatatatt tacaaataca caagttatcc tgaccctata    660
ttgttgatga aaagtgctag aaatagttgt tggtctaaag atgcagaata tggactctat    720
tccatctatc aaggggaat atttgagctt aaggaaaatg acagaatttt tgtttctgta    780
```

```
acaaatgagc acttgataga catggaccat gaagccagtt ttttcggggc cttttttagtt    840 ggctaa                                                                846
```

The invention claimed is:

1. A method of obtaining a modified line of NK-cells with a knockout of the PD-1 gene in order to inactivate the expression of the PD-1 gene, comprising:
   A) selecting at least one guide RNA sequence specific to the PD-1 gene, the guide RNA sequence being selected from the group consisting of: SEQ ID NO: 1, SEQ ID NO: 2, SEQ ID NO: 3, and SEQ ID NO: 4;
   B) constructing separate expression plasmid vectors encoding each of the selected guide RNA sequences and an endonuclease Cas9;
   C) synthesizing a fragment of donor DNA encoding one of:
      i) an expression cassette for Fas-ligand having the sequence according to SEQ ID NO: 16, or
      ii) an expression cassette for TRAIL having the sequence according to SEQ ID NO: 20, or
      iii) an expression cassette for resistance of cells to zeocin having the sequence according to SEQ ID NO: 9;
   D) transfecting a culture of NK-cells with at least one of the expression plasmid vectors of B) and with the donor DNA of C);
   E) staining the NK-cells with anti-PD-1 antibodies and anti-Fas-ligand antibodies, or staining the NK-cells with anti-PD-1 antibodies and anti-TRAIL antibodies, or culturing the NK-cells in a selective medium with zeocin and staining the surviving cells with anti-PD-1 antibodies;
   F) carrying out a selection and cloning of cells with a minimum signal for PD-1 and a maximum signal for Fas-ligand or for TRAIL using a flow sorter, or carrying out a selection and cloning of zeocin-cultured cells with a minimum signal for PD-1 using a flow sorter; and
   G) carrying out a secondary cultivation of cell clones and selection of cells using immunoblotting with anti-PD-1 antibodies and anti-Fas-ligand antibodies, or with anti-PD-1 antibodies and anti-TRAIL antibodies, or with anti-PD-1 antibodies.

2. The method according to claim 1, wherein at least one of the expression plasmid vectors includes: 295-572 bp—CBh promoter; 819-5090 bp—Cas9 endonuclease; 5121-5328 bp—Poly A Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

3. The method of according to claim 1, wherein at least one of the expression plasmid vectors includes: 295-572 bp—CBh promoter; 819-5090 bp—Cas9 endonuclease; 5121-5328 bp—Poly A Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

4. The method according to claim 1, wherein the donor DNA encoding the expression cassette for resistance of cells to zeocin includes:
   a fragment containing the sequence of the first part of the PD-1 gene with a size of 379 base pairs, characterized by the nucleotide sequence shown in SEQ ID NO: 10;
   a fragment containing the sequence of CMV enhancer with a size of 405 base pairs, characterized by the nucleotide sequence shown in SEQ ID NO: 11;
   a fragment containing the sequence-hFerL Promoter with a size of 263 base pairs, characterized by the nucleotide sequence shown in SEQ ID NO: 12;
   a fragment containing the sequence-Zeo-zeocin resistance gene with a size of 375 base pairs, characterized by the nucleotide sequence shown in SEQ ID NO: 13;
   a fragment containing the sequence pGlo poly A Signal with a size of 401 base pairs, characterized by the nucleotide sequence shown in SEQ ID NO: 14; and
   a fragment containing the sequence of the second part of the PD-1 gene with a size of 276 base pairs and characterized by the nucleotide sequence shown in SEQ ID NO: 15.

5. The method according to claim 1, wherein at least one of the expression plasmid vectors includes: 295-572 bp—CBh promoter; 819-5090 bp—Cas9 endonuclease; 5121-5328 bp—Poly A Signal; 5552-6007 bp—P ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

6. The method according to claim 1, wherein the donor DNA encoding the expression cassette for Fas-ligand includes:
   a fragment containing the sequence of the first part of the PD-1 gene with a size of 379 base pairs, characterized by the nucleotide sequence shown in SEQ ID NO: 10;
   a fragment containing the sequence CMV Promoter with a size of 588 base pairs, characterized by the nucleotide sequence shown in SEQ ID NO: 17;
   a fragment containing the sequence Fas-ligand with a size of 846 base pairs characterized by the nucleotide sequence shown in SEQ ID NO: 18;
   a fragment containing the sequence BGH Poly A Signal with a size of 225 base pairs, characterized by the nucleotide sequence shown in SEQ ID NO: 19; and
   a fragment containing the sequence of the second part of the PD-1 gene with a size of 276 base pairs, characterized by the nucleotide sequence shown in SEQ ID NO: 15.

7. The method according to claim 1, wherein at least one of the expression plasmid vectors includes: 295-572 bp—CBh promoter; 819-5090 bp—Cas9 endonuclease; 5121-5328 bp—Poly_A Signal; 5552-6007 bp—fl ori; 6289-6393 bp—bla promoter; 6394-7254 bp—bla; 7425-8013 bp—ColE1 ori; 8075-8315 bp—U6 promoter; and 8322-8419 bp—sequence encoding a guide RNA.

8. The method according to claim 1, wherein the donor DNA encoding the expression cassette for TRAIL includes:
   a fragment containing the sequence of the first part of the PD-1 gene with a size of 379 base pairs, characterized by a nucleotide sequence presented in SEQ ID NO: 10;
   a fragment containing the sequence CMV Promoter with a size of 588 base pairs, characterized by the nucleotide sequence shown in SEQ ID NO: 17;
   a fragment containing the sequence TRAIL with a size of 846 base pairs, characterized by the nucleotide sequence shown in SEQ ID NO: 21;

a fragment containing the sequence BGH Poly A Signal with a size of 225 base pairs, characterized by the nucleotide sequence shown in SEQ ID NO: 19; and a fragment containing the sequence of the second part of the PD-1 gene with a size of 276 base pairs, characterized by the nucleotide sequence shown in SEQ ID NO: 15.

9. A method of inducing apoptosis or lysis of mammalian cancer cells, the method comprising administering an effective amount of a NK-cell obtained from the modified NK-cell line of claim 1 to a mammal.

* * * * *